United States Patent
Meeusen et al.

(10) Patent No.: US 12,313,615 B2
(45) Date of Patent: May 27, 2025

(54) APPARATUS AND METHOD FOR MEASURING WATER QUALITY IN A WATER DISTRIBUTION SYSTEM

(71) Applicant: Badger Meter, Inc., Milwaukee, WI (US)

(72) Inventors: Richard A. Meeusen, Pewaukee, WI (US); Gregory A. Gomez, Waukesha, WI (US); James Donald Faber, Tulsa, OK (US); Dennis J. Webb, Glendale, WI (US); Daniel D. Zandron, Sussex, WI (US); Mark Lazar, New Berlin, WI (US)

(73) Assignee: Badger Meter, Inc, Brown Deer, WI (US)

( * ) Notice: Subject to any disclaimer, the term of this patent is extended or adjusted under 35 U.S.C. 154(b) by 431 days.

(21) Appl. No.: 16/587,472

(22) Filed: Sep. 30, 2019

(65) Prior Publication Data

US 2020/0033313 A1    Jan. 30, 2020

Related U.S. Application Data

(63) Continuation of application No. 15/013,558, filed on Feb. 2, 2016, which is a continuation of application
(Continued)

(51) Int. Cl.
 *G01N 33/18* (2006.01)
 *G01F 1/56* (2006.01)
 *G01N 35/00* (2006.01)

(52) U.S. Cl.
 CPC ............... *G01N 33/18* (2013.01); *G01F 1/56* (2013.01); *G01N 35/00871* (2013.01); *Y10T 436/20* (2015.01)

(58) Field of Classification Search
 CPC .... G01F 1/56; G01N 33/18; G01N 35/00871; Y10T 436/20; B01J 19/0046; B01J 2219/00722; B01L 2300/0816
(Continued)

(56) References Cited

U.S. PATENT DOCUMENTS 4,386,157 A * 5/1983 Nishioka ......................... 435/39
4,626,992 A   12/1986 Greaves et al.
(Continued)

FOREIGN PATENT DOCUMENTS

WO    WO-2006135849 A2 * 12/2006    ............. G01N 33/18
WO    WO2015097405        * 7/2015

OTHER PUBLICATIONS

Ashim Banerjee et al., "Water Distribution System Security—An Urgent Need," Real-Time Monitoring Using Micro-Sensor Networks, Colorado State University, Apr. 12, 2006, pp. 1-4.

*Primary Examiner* — John Fitzgerald
*Assistant Examiner* — Truong D Phan
(74) *Attorney, Agent, or Firm* — Boyle Fredrickson SC

(57) ABSTRACT

A water quality monitoring computer system for a water distribution network includes a water distribution network configured to receive water from one or more network sources and distribute the water through the water distribution network to one or more network end points, at least one water quality monitor configured to generate water quality data for a distribution zone of the water quality network that includes a zone water source and one or more zone endpoints, which includes network end points downstream from the zone source, and a zone end point meter associated with each of the zone end points, wherein the zone end point meter monitors water flow exiting the distribution zone. At least two of the end point water meters include one or more water quality sensors and at least two of the end point water meters include different water quality sensor types, and the
(Continued)

one water quality monitor aggregates water quality sensor data transmitted from the zone end point water meters to generate the distribution zone water quality data.

16 Claims, 2 Drawing Sheets

Related U.S. Application Data

No. 12/891,963, filed on Sep. 28, 2010, now abandoned, which is a continuation of application No. 12/439,258, filed as application No. PCT/US2008/070052 on Jul. 15, 2008, now abandoned.

(60) Provisional application No. 60/959,833, filed on Jul. 17, 2007.

(58) Field of Classification Search
USPC ............ 73/861.08; 422/68.1; 340/870.01, 340/870.02, 870.03
See application file for complete search history.

(56) References Cited

U.S. PATENT DOCUMENTS

| | | |
|---|---|---|
| 5,646,863 A | 7/1997 | Morton |
| 6,245,224 B1 | 6/2001 | Enoki et al. |
| 6,290,908 B1 | 9/2001 | Fukunaga et al. |
| 6,398,930 B2 | 6/2002 | Fukunaga et al. |
| 6,444,172 B2 | 9/2002 | Fukunaga et al. |
| 6,747,571 B2 | 6/2004 | Fierro et al. |
| 6,753,186 B2 | 6/2004 | Moskoff |
| 7,104,115 B2 | 9/2006 | Kahn et al. |
| 7,249,000 B2 * | 7/2007 | Kahn ............................ 702/188 |
| 7,289,923 B2 | 10/2007 | Marovitz |
| 7,454,295 B2 | 11/2008 | Wolfe |
| 7,497,957 B2 | 3/2009 | Frank |
| 2004/0006513 A1 * | 1/2004 | Wolfe ..................... G06G 1/14 705/22 |
| 2004/0069345 A1 | 4/2004 | Doan |
| 2005/0247113 A1 | 11/2005 | Kahn et al. |
| 2005/0272372 A1 | 12/2005 | Rodriguez |
| 2007/0021936 A1 | 1/2007 | Marovitz |
| 2007/0070356 A1 | 3/2007 | Tan et al. |
| 2007/0090059 A1 | 4/2007 | Plummer et al. |
| 2007/0233397 A1 * | 10/2007 | Kim ................................ 702/19 |
| 2007/0284293 A1 * | 12/2007 | Pitchford .................. G01F 3/12 210/85 |
| 2008/0109175 A1 * | 5/2008 | Michalak ................ C02F 1/008 702/50 |
| 2013/0113631 A1 * | 5/2013 | Pitchford .................. H02J 7/34 340/870.02 |

* cited by examiner

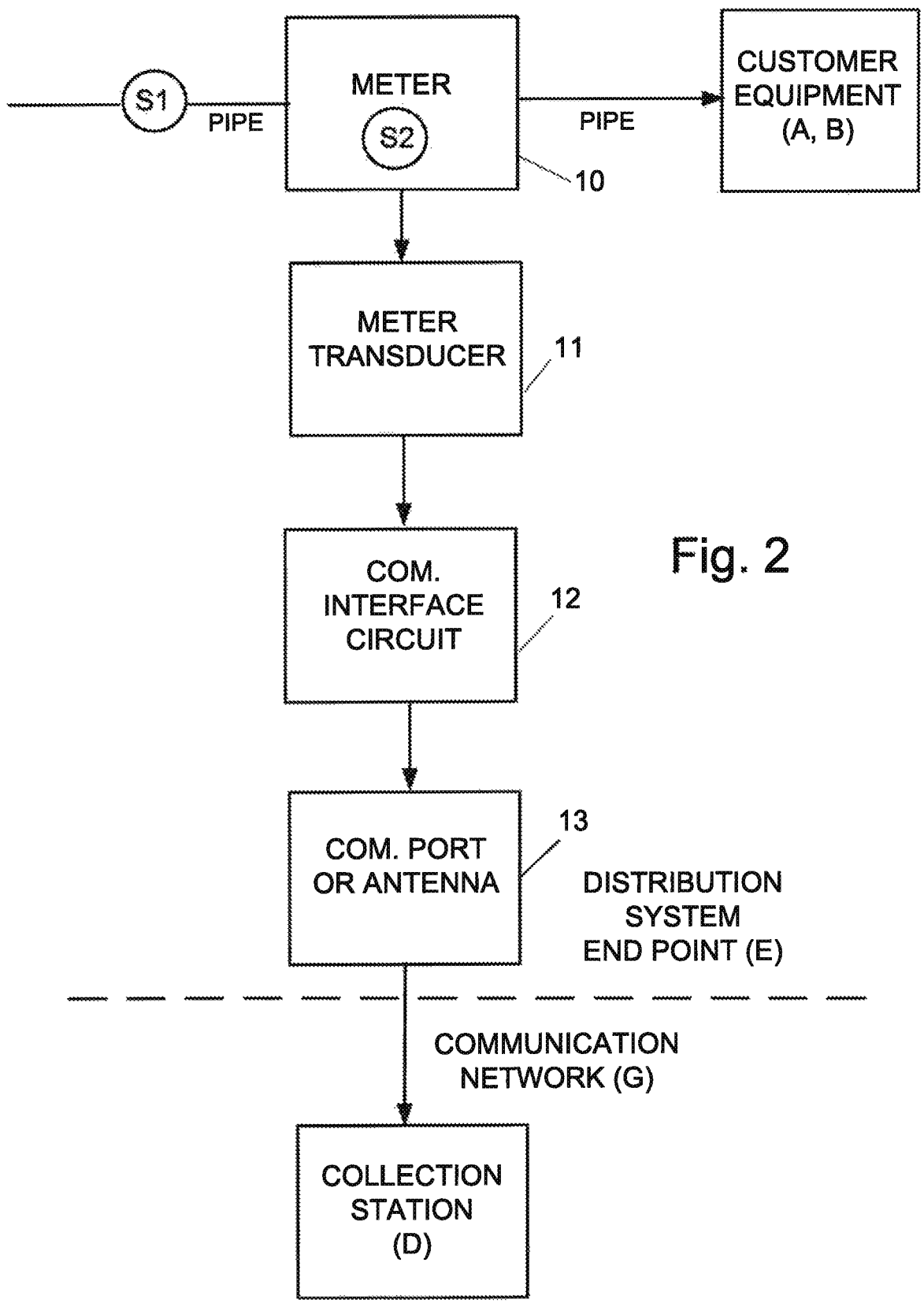

APPARATUS AND METHOD FOR MEASURING WATER QUALITY IN A WATER DISTRIBUTION SYSTEM

CROSS REFERENCE TO RELATED APPLICATIONS

This application is a continuation of U.S. patent application Ser. No. 15/013,558, filed Feb. 2, 2016, which is a continuation of U.S. patent application Ser. No. 12/891,963, filed Sep. 28, 2010, which is a continuation of U.S. patent application Ser. No. 12/439,258, filed Feb. 27, 2009, which was a 371 of PCT/US08/070052, filed Jul. 15, 2008 which claims the benefit of priority based on U.S. Prov. Pat. App. No. 60/959,833, filed Jul. 17, 2007, all of which are hereby incorporated by reference herein.

TECHNICAL FIELD

The field of the invention is meter data collection systems for metering consumption of water supplied to single-unit residential, multi-unit residential, commercial and industrial customers from a municipal or district utility provider. The invention also relates to instruments for sensing water quality in such a meter data collection system.

BACKGROUND OF THE INVENTION

Current methods and practices for sensing water quality through biological and chemical parameters, as well as environmental parameters such as residual chlorine, TOC (total organic carbon), turbidity, pressure, and others, involve systems with expensive sensors located at special stations within a water system. Many systems currently available on the market to test for environmental parameters require a waste stream, sometimes toxic, as a byproduct of the testing. This methodology cannot be used at the end points of a utility distribution network. Also, the systems provided today provide sensing of several environmental parameters at one time. These systems are installed at source water, underground tanks and elevated tank locations. It has not been economically or environmentally practical to install these systems at end point locations in a water metering system.
network. If this were to occur, it is probable the current technologies and equipment would not detect the contamination event.

SUMMARY OF THE INVENTION

The invention provides a method for the sensing of various biological and chemical contaminants and environmental parameters at the end points of a water utility metering network.

In the system of the invention, a water quality monitoring computer system for a water distribution network includes a water distribution network configured to receive water from one or more network sources and distribute the water through the water distribution network to one or more network end points, at least one water quality monitor configured to generate water quality data for a distribution zone of the water quality network that includes a zone water source and one or more zone endpoints, which includes network end points downstream from the zone source, and a zone end point meter associated with each of the zone end points, wherein the zone end point meter monitors water flow exiting the distribution zone. At least two of the end point water meters include one or more water quality sensors and at least two of the end point water meters include different water quality sensor types, and the one water quality monitor aggregates water quality sensor data transmitted from the zone end point water meters to generate the distribution zone water quality data.

A water utility distribution system can be protected from a wide array of potential biological and chemical contaminants and environmental parameters and can be economically deployed using the present invention, as there is only one parameter sensed per meter. It also provides early automatic detection of potential contamination events.

The invention can be used to provide a first indication of contamination from which further field or lab testing can be performed to confirm anomalous conditions.

Other objects and advantages of the invention, besides those discussed above, will be apparent to those of ordinary skill in the art from the description of the preferred embodiments which follows. In the description, reference is made to the accompanying drawings, which form a part hereof, and which illustrate examples of the invention.

BRIEF DESCRIPTION OF THE DRAWING

FIG. 2 is a block diagram of an apparatus at a single metering end point.

DETAILED DESCRIPTION

Figure 1:
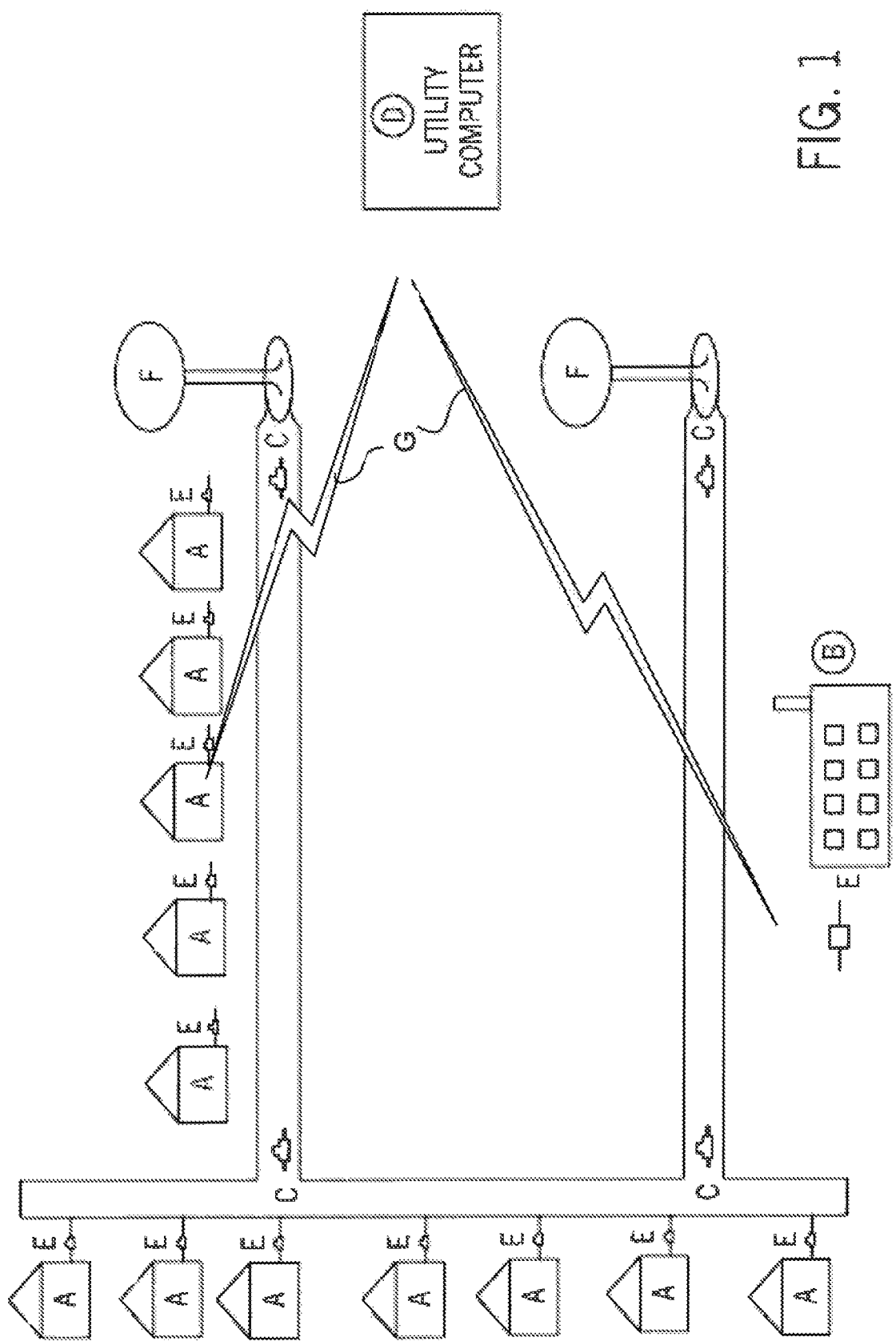
FIG. 1 is schematic diagram of a water utility distribution and water metering system incorporating the present invention.

FIG. 1 illustrates a subsection of a water utility distribution system, where "A" designates individual single-unit end points within the distribution system. "B" designates individual commercial, industrial or multi-unit end points within the distribution system. "C" designates zone water meters that measure the quantity or quality of water distributed to one zone or section of the distribution system. "D" designates the utility main office computer system. "E" designates the end point meters that measure the quantity or quality of water distributed to a single Residential, commercial or industrial end point. "F" designates a water storage facility (tanks or vaults) for water used within the distribution system, And, "G" designates a wireless network such as SMS, GPRS, GSM, private radio network, PSTN, or wireless Internet.

Currently, water utilities must report several parameters to a governmental environmental protection agency on a quarterly basis. These parameters include chlorine residual, TOC (total organic carbon), dissolved oxygen, etc. To accomplish this reporting, utilities typically take water samples from various locations throughout the distribution system and send these samples to a laboratory for analysis of parametric testing. An alternate method is the installation of expensive computer controlled systems that automatically take samples from each location and provide parametric analysis.

While these systems provide more data on a more frequent basis, they have a waste stream that requires maintenance and special handling. As they are expensive, most utilities are limited to installations at source water locations or storage facilities, and the equipment is not distributed throughout the distribution system.

In the present invention, individual sensors monitor respective parameters and are co-located with a meter, as illustrated by C or E in the illustration. Meters, illustrated as the element E, typically measure quantity of water consumed at a single end point within the distribution system. These meters can also be assembled with, or connected to, one or more sensors to measure the quality of water supplied to the single end point. It is often advantageous to take readings from several places in the distribution system due to different concentrations of substances due to dilution. Likewise, zone meters, illustrated as the element C, typically measure quantity of water consumed with a specific zone, or section, of the distribution system. When fitted with one or more sensors, these meters could provide water quality readings for an entire zone, or section. Also, a set of sensors for measuring or detecting respective chemical, biological and environmental parameters can be arranged to measure different parameters within a zone of the distribution system, thus providing coverage for many parameters.

Consumption and water quality data can be transmitted wirelessly to a collection station, such as a utility computer, D, over a wireless network, G, such as SMS, GPRS, GSM, private radio network, PSTN, or wireless Internet. Water quality reporting to the EPA could then be completed on a real-time basis, instead of on a quarterly or semi-annually.

FIG. 2 illustrates the components of a single distribution end point apparatus E at customer locations, A and B. As shown there, a meter 10 is connected in a pipe supplying water to the customer equipment at sites A, B. The parameter sensor can be a sensor S1 mounted in or on the pipeline near the meter 10, or it can be sensor S2 integrated into the meter 10. The meter 10 communicates with a communication interface circuit 12 through a transducer 11 which may convert movements of a magnet to electrical signals. It also feasible to use electronic meters which produce an electrical signal directly to the circuit 12. The sensors S1 and S2 also communicate electrical sensing signals to the communication interface circuit 12. This circuit 12 converts device input signals to data and in this embodiment, modulates a carrier wave with information signals representing the data, so that a radio signal can be transmitted over a wireless network through an antenna 13. It is also possible for the communication interface circuit to transmit data signals through a communication port 13 to an external modulator/ antenna unit. In either situation, radio signals encoded with metering data, including sensor data, are transmitted back to the collection station D including the utility computer seen in FIG. 1.

The electronic circuitry 12 within the end point (meter) can in some embodiments poll the microsensor S2 that resides within the meter 10 in the flow stream. When the electronic circuitry detects an anomalous condition from the sensor, a tamper flag is set and an alarm transaction is transmitted to the collections station D via the communication interface circuit 12. Upon notification of the anomalous condition, utility personnel will know which potential contaminant has been detected because of the identification number of the end point that transmits the alarm transaction. The water utility can then go to the source for further field testing to validate the contamination event.

Other sensors fitted into meters can be for first level detection of various bio-toxins, chemical toxins or other hazardous substances. This first level detection could greatly improve the response time and public notification of hazardous events.

The system components at each meter C and E can be further described as follows.

Microelectronic sensors S1 and S2 are located at an end point (meter) within the flow stream of a water utility distribution system. A parameter sensor detects the presence or threshold of a single respective biological, chemical or environmental parameter (e.g. TOC or dissolved oxygen). Each sensor with a zone detects a different respective biological, chemical or environmental parameter. As the sensor is located in the supply flow stream, the system does not have a waste stream.

The flow meter 10 is located at the lowest point in the distribution system where the utility would like to measure the quantity of water. Also, the meter 10 may be the lowest point within the distribution system where the utility desires to measure the quality of water. In this case, the parameter sensors S1, S2 would be located near or inside the meter 10. In cases where water quantity and quality are important at that location the meter would measure the amount of water to pass through it and house the parameter sensor to measure the quality of the water passing through it.

There is typically a transducer 11 for converting mechanical movement of the flow meter to electrical signals, a memory to store readings and transmitter circuitry 12, 13 for transmitting electrical signals to a remote receiver. This transmitter can be part of a transceiver for receiving RF signals as well as transmitting RF signals. In cases where water quality is sensed at the meter 10, the circuitry 11, 12 and 13 would also read and act on water quality data and alarm conditions from the parameter sensor and transmit these to a remote receiver. Many AMR systems are known for transmitting utility consumption data from the end points (E) to a central location (D) for processing. Such systems can be modified to communicate and process water quality data as well. The zone meters (C) can also be provided with this type of electronic signaling equipment. The water quality data from various locations within the system can then be collected at the collection station D for further processing to determine water quality on a system basis.

This has been a description of the preferred embodiments, but it will be apparent to those of ordinary skill in the art that modifications may be made in the details of these specific embodiments. Such modifications are intended to be encompassed by the broadest aspects of the present invention unless excluded by the following claims.

What is claimed is:

1. A water quality monitoring computer system for a water distribution network, comprising:
   a water distribution network configured to receive water from one or more network sources and distribute the water through the water distribution network to one or more network end points;
   at least one water quality monitor configured to generate water quality data for a distribution zone of the water quality network that includes a zone water source and one or more zone endpoints, which includes network end points downstream from the zone source; and
   a zone end point meter associated with each of the zone end points, wherein the zone end point meter monitors water flow exiting the distribution zone;
   wherein at least two of the end point water meters include a single water quality sensor and each end point water meter includes a different water quality sensor type,
   wherein the one water quality monitor aggregates water quality sensor data transmitted from the zone end point water meters to generate the distribution zone water quality data.

2. The system of claim 1, further including a zone source meter at the zone source, the zone source meter including at least one zone water quality sensor that is a different type from the water quality sensors in the zone end point water meters.

3. The system of claim 2, wherein all of the end point water meters in the distribution zone are downstream in the water distribution system from the zone water meter.

4. The system of claim 1, wherein the water quality data includes a residual chlorine value, a total organic carbon value and a dissolved oxygen value.

5. The system of claim 1, wherein the water quality data is transmitted to the environmental protection agency in real time.

6. The system of claim 1, wherein the different water quality sensor types include at least one chemical sensor type, one biological sensor type and one environmental sensor type.

7. The system of claim 1, wherein the data transmitted from the zone end point meters to the water quality monitor includes sensor data and water consumption data.

8. The system of claim 1, wherein each zone end point meter is configured to include a single water quality sensor that is unique to that zone end point meter.

9. A computer-implemented method for generating water quality data for a water distribution zone in a water distribution network, comprising:
receiving end point water quality data from a plurality of zone end point meters, each zone end point meter associated with a zone end point, wherein the each zone end point meter monitors water flow exiting the water distribution network and includes a single water quality sensor of a sensor type that is unique within the water distribution zone to generate end point water quality data; and
determining water quality data for the water distribution zone based at least in part on an aggregation of the end point water quality data, wherein a zone source meter monitors water flow entering the water distribution zone.

10. The computer-implemented method of claim 9, wherein the water quality data includes data from a third type of water quality sensor included in the zone source meter.

11. The computer-implemented method of claim 10, wherein all of the end point water meters in the distribution zone are downstream in the water distribution system from the zone water meter.

12. The computer-implemented method of claim 9, wherein the water quality data includes a residual chlorine value, a total organic carbon value and a dissolved oxygen value.

13. The computer-implemented method of claim 9, wherein the water quality data is transmitted to the environmental protection agency in real time.

14. The computer-implemented method of claim 9, wherein the different water quality sensor types include at least one chemical sensor type, one biological sensor type and one environmental sensor type.

15. The computer-implemented method of claim 9, wherein the data transmitted from the zone end point meters includes sensor data and water consumption data.

16. The computer-implemented method of claim 9, wherein each zone end point meter is configured to include a single water quality sensor that is unique to that zone end point meter.

* * * * *